United States Patent [19]

Shimizu et al.

[11] Patent Number: 5,436,402
[45] Date of Patent: Jul. 25, 1995

[54] METHOD FOR PREPARING P-ISOBUTYLSTYRENE

[75] Inventors: Isoo Shimizu; Yasuo Matsumura; Yuichi Tokumoto; Kazumichi Uchida, all of Yokohama, Japan

[73] Assignee: Nippon Petrochemicals Co., Ltd., Tokyo, Japan

[21] Appl. No.: 323,600

[22] Filed: Oct. 17, 1994

Related U.S. Application Data

[63] Continuation of Ser. No. 62,703, May 14, 1993, abandoned, which is a continuation of Ser. No. 917,799, Jul. 20, 1992, abandoned, which is a continuation of Ser. No. 435,776, Nov. 13, 1989, abandoned.

[30] Foreign Application Priority Data

Dec. 13, 1988 [JP] Japan .................. 63-314153

[51] Int. Cl.$^6$ .................. C07C 5/27; C07C 5/333
[52] U.S. Cl. .................. 585/321; 585/322; 585/440; 585/444; 585/445; 585/470
[58] Field of Search ........... 585/321, 440, 444, 445, 585/470

[56] References Cited

U.S. PATENT DOCUMENTS

| | | | |
|---|---|---|---|
| 2,443,217 | 7/1945 | Amos et al. | 585/440 |
| 3,179,706 | 4/1965 | Lee | 585/445 |
| 3,435,086 | 3/1969 | Soderquist | 585/445 |
| 3,631,213 | 12/1971 | Brewer | 585/445 |
| 4,052,474 | 10/1977 | McClure | 585/470 |
| 4,128,592 | 12/1978 | Kaeding | 585/471 |
| 4,329,507 | 5/1982 | Takeda et al. | 585/435 |
| 4,370,508 | 1/1983 | Kaeding | 585/467 |
| 4,375,575 | 3/1983 | Slaugh | 585/480 |
| 4,420,649 | 12/1983 | Antos | 585/434 |
| 4,454,364 | 6/1984 | Farcasiu et al. | 585/470 |
| 4,504,690 | 3/1985 | Forbus et al. | 585/467 |
| 4,590,324 | 5/1986 | Sater | 585/444 |
| 4,723,051 | 2/1988 | Menard et al. | 585/481 |
| 4,827,065 | 5/1989 | Shimizu et al. | 585/25 |
| 4,855,518 | 8/1989 | Shimizu et al. | 585/319 |
| 4,861,740 | 8/1989 | Sachtler et al. | 502/66 |
| 5,026,939 | 6/1991 | Shimizu et al. | 585/439 |

FOREIGN PATENT DOCUMENTS

| | | | |
|---|---|---|---|
| 1109164 | 6/1961 | Germany . | |
| 59-35899 | 2/1984 | Japan | B23K 35/40 |

OTHER PUBLICATIONS

Badr, J. *Appln. Chem. Biotech.*, 22, 967–972 (1972).

*Primary Examiner*—Asok Pal
*Attorney, Agent, or Firm*—Scully, Scott, Murphy & Presser

[57] ABSTRACT

A method for preparing a high-purity p-isobutylstyrene is here disclosed which comprises the first step of reacting o- and/or m-isobutylethylbenzene, if necessary, together with isobutylbenzene, in the presence of an acid catalyst in a liquid phase at a reaction temperature of $-10°$ to $600°$ C. so that the production of sec-butylethylbenzene in butylethylbenzene may not exceed 20% by weight, in order to form a mixture of p-isobutylethylbenzene and sec-butylethylbenzene; and the second step of bringing the mixture of p-isobutylethylbenzene and sec-butylethylbenzene recovered from the first step into contact with a dehydrogenation metal catalyst containing at least one metal selected from the groups Ib, IIb, VIa, VIIa and VIII of the periodic table at a reaction temperature of $300°$ to $650°$ C. under a reaction pressure of 50 kg/cm$^2$ or less in a gaseous phase.

15 Claims, No Drawings

METHOD FOR PREPARING P-ISOBUTYLSTYRENE

This is a continuation of application Ser. No. 08/062,703 filed on May 14, 1993 now abandoned, which is a File-Wrapper Continuation application of U.S. Ser. No. 07/917,799 filed Jul. 20, 1992 now abandoned; which is a File-Wrapper Continuation application of U.S. Ser. No. 07/435,776 filed Nov. 13, 1989, now abandoned.

BACKGROUND OF THE INVENTION

1. Field of the Invention

The present invention relates to a method for preparing high-purity p-isobutylstyrene. More specifically, it relates to a method for preparing high-purity p-isobutylstyrene by first subjecting o- and/or m-isobutylethylbenzene, which is a novel substance, to a dispropornation reaction to form p-isobutylethylbenzene, and then dehydrogenating the latter.

p-Isobutylstyrene is useful as an intermediate which can be utilized to inexpensively and economically manufacture α-(4-isobutylphenyl)propionic acid (trade name Ibuprofen) which is important as a medicine such as an anti-inflammatory drug or the like.

2. Description of the Prior Art

Heretofore, α-(4-isobutylphenyl)propionic acid has been synthesized by various suggested methods. One of these suggested methods comprises subjecting p-isobutylstyrene to a hydroformylation reaction or a Reppe reaction (Japanese Laid-open Patent Application Nos. 51338/1977, 6233/1977, 97930/1977 and 10545/1984).

This method for preparing α-(4-isobutylphenyl)propionic acid from p-isobutylstyrene is economically excellent, because p-isobutylstyrene which is a starting material is a simple and stable compound and the hydroformylation reaction or the Reppe reaction does not consume any expensive reagents and the like.

It is known that p-isobutylstyrene is manufactured by hydrogenating p-isobutylacetophenone, followed by dehydrating, as disclosed in Japanese Patent Publication No. 35899/1984. Furthermore, p-isobutylstyrene can be also manufactured by first reacting isobutylbenzene with acetaldehyde in the presence of a sulfuric acid catalyst to form 1,1-bis(p-isobutylphenyl)ethane, and then decomposing the latter in the presence of an acid catalyst, as disclosed in Japanese Laid-open Patent Application No. 24527/1986. In these methods, however, many steps are necessary, a great deal of the catalyst is consumed, and the used waste catalyst is too strong in acidity to easily throw away, which increases the manufacturing cost of p-isobutylstyrene.

In view of the above-mentioned situations, the inventors of the present application, as a result of intensive researches, have developed a method for preparing p-isobutylstyrene by selectively dehydrogenating only the ethyl group of p-isobutylethylbenzene.

However, with regard to the manufacturing methods of p-isobutylethylbenzene, there are merely a very few conventional techniques, and according to one example described in Beilstein, EIV5 (Sys. Nr. 470/H445), 1-(4-ethylphenyl)-2-methylpropane-1-one is reduced with potassium hydroxide and hydrazine in a diethylene glycol solvent to produce p-isobutylethylbenzene. In this method, however, 1-(4-ethylphenyl)-2-methylpropane-1-one which is the raw material is very expensive, and hydrazine which must be used as the reducing agent is very dangerous in treating. They impede the industrialization of this method. Moreover, it is also known that p-isobutylethylbenzene can be produced as a by-product of the catalytic decomposition reaction of 1,1-bis(p-isobutylphenyl)ethane, as disclosed in examples in Japanese Laid-open Patent Application No. 37743/1986, but this method is not preferable, because p-isobutylethylbenzene is only the by-product and thus its productivity is extremely low.

For these reasons, another economical method for the manufacture of p-isobutylstyrene is desired. Thus, the present inventors have further advanced the researches, and as a result, they have developed a method for preparing p-isobutylethylbenzene by the utilization of alkylation. That is, one example of this method comprises ethylating isobutylbenzene. In this case, position selectivity in the ethylation is not usually high, and so the ethylation gives the production of o- and m-position isomers in addition to a p-position isomer. In this case, p-isobutylethylbenzene can be collected by separation, but it is uneconomical that the separated o- and m-isobutylethylbenzenes are thrown away. In addition, useful applications for o- and m-isobutylethylbenzenes have not been known yet.

Here, the present inventors have tried disproportionating o- and m-isobutylethylbenzenes by the use of an acid catalyst to convert them into p-isobutylethylbenzene.

However, when the dispropornation reaction is carried out in the presence of the acid catalyst, the skeleton isomerization of an isobutyl group in isobutylethylbenzene also takes place. It is extremely difficult to separate secondary butylethylbenzene produced by the skeleton isomerization from isobutylethylbenzene which is its isomer, because boiling points of these compounds are close to each other.

From the above-mentioned viewpoint, the present inventors have advanced the researches, and eventually the present invention has now been achieved.

SUMMARY OF THE INVENTION

An object of the present invention is to provide a method for preparing p-isobutylstyrene having useful applications in a high purity from o- or m-isobutylethylbenzene which is a novel substance and which is not useful.

That is, the present invention is directed to a method for preparing a high-purity p-isobutylstyrene which comprises the first step of reacting o- and/or m-isobutylethylbenzene, if necessary, together with isobutylbenzene, in the presence of an acid catalyst at a reaction temperature of −10° to 600° C. so that the production of sec-butylethylbenzene in butylethylbenzene may not exceed 20% by weight, in order to form a mixture of p-isobutylethylbenzene and sec-butylethylbenzene; and the second step of bringing the mixture of p-isobutylethylbenzene and sec-butylethylbenzene recovered from the first step into contact with a dehydrogenation metal catalyst containing at least one metal selected from the groups Ib, IIb, VIa, VIIa and VIII of the periodic table at a reaction temperature of 300° to 650° C. under a reaction pressure of 50 kg/cm$^2$ or less in a gaseous phase.

Now, the present invention will be described in detail.

The present inventors have found that when o-isobutylethylbenzene, m-isobutylethylbenzene or a mixture thereof is disproportionated by a disproportionation catalyst comprising an acid catalyst, p-isobutylethylbenzene is produced.

With regard to the acid catalyst which is effective for the disproportionation, examples of the solid acid catalyst include synthetic catalysts such as silica-alumina and silica-magnesia, and natural clay minerals such as acidic China clay and active China clay. A zeolite can be also used, and examples of the zeolite are hydrogen zeolites such as HX type zeolites, HY type zeolites and hydrogen faujasite. These hydrogen zeolites exhibit strong acidity, and each of these zeolites is what is obtained by converting a part or all of an alkali metal salt of a zeolite such as NaX zeolite, NaY zeolite or Na faujasite into a proton type by cation exchange. In addition, a strong acid type cation exchanger resin such as perfluorosulfonic acid resin (trade name Naphion) can be used. Examples of an organic acid catalyst include trifluoromethansulfonic acid and p-toluenesulfonic acid, and examples of an inorganic acid catalyst include hydrochloric acid, sulfuric acid and hydrogen fluoride. A Friedel-Crafts catalyst can be also used, and examples of this kind include metal halides such as aluminum chloride, iron bromide, titanium chloride and boron trifluoride. Moreover, heteropoly-acids such as phosphotungstic acid, phosphomolybdic acid, silicotungstic acid and silicomolybdic acid are also effective as the catalysts. The heteropoly-acid is an acid substance comprising oxides of a poly-atom such as molybdenum or tungsten and a hetero-atom, and examples of the hetero-atom include P, B, V, As, Si, Ge, Sn, Ti, Zr, Ce, Th, Fe, Pt, Mn, Co, Ni, Te, I, Al, Cr, Rh, Cu and Se.

In the present invention, the above-mentioned acid catalysts may be used singly or in a suitable combination of two or more thereof, and they may be supported on a suitable carrier, when used. Typical examples of such a type include supported acid catalysts obtained by supporting the above-mentioned acid materials on carriers mainly comprising a porous inorganic material such as alumina, magnesia, silica and active carbon.

The raw material which will be subjected to the disproportionation reaction is o- or m-isobutylethylbenzene or a mixture thereof. One example of such a mixture is a fraction containing o- and m-isobutylethylbenzene which is left after p-isobutylethylbenzene has been separated and recovered from isobutylbenzene ethylated with ethylene. Even if this mixture contains isobutylpolyethylbenzene such as isobutyldiethylbenzene or isobutyltriethylbenzene, the above-mentioned object of the present invetnion is not affected at all.

If desired, isobutylbenzene may be present in the reaction system. The amount of this isobutylbenzene can be suitably decided.

The reaction temperature in the dispropotionation step should be selected from the range of $-10°$ to $600°$ C. so that the amount of sec-butylethylbenzene may not exceed 20% by weight, preferably 10% by weight with respect to the total weight of butylethylbenzene in the product. This reaction temperature depends upon a kind of acid catalyst to be used. For example, in the case that a solid inorganic acid such as silica-alimina or a heteropoly-acid catalyst is used, the optimum reaction temperature is in the range of $120°$ to $450°$ C.; in the case of a hydrogen zeolite catalyst, it is from $120°$ to $350°$ C.; in the case of a strong acid type cation exchanger catalyst, it is from $-5°$ to $250°$ C.; in the case of an organic superstrong acid catalyst such as hydrogen fluoride or trifluoromethanesulfonic acid, it is from $-10°$ to $200°$ C.; and in the case of a metal halide such as aluminum chloride, it is from $-5°$ to $80°$ C.

If the reaction temperature is less than the lower limit of the above-mentioned temperature range, a reaction rate is low, though the production of sec-butylethylbenzene is inhibited to a low level. In order to heighten the reaction ratio of the disproportionation, a long period of reaction time is required, so that efficiency is too low to be practicable. Inversely, if the reaction temperature is higher than the upper limit of the above-mentioned temperature range, the skeleton isomerization reaction of the isobutyl group increases, so that the ratio of sec-butylethylbenzene to the total weight of butylethylbenzene such as isobutylethylbenzene and sec-butylethylbenzene in the product is in excess of 20% by weight unpreferably. In addition, decomposition which is a secondary reaction takes place, so that the yield of the desired product also decreases unpreferably.

Usually, even if the reaction temperature is controlled as described above, it is difficult to perfectly inhibit the production of sec-butylethylbenzene. That is, so long as the disproportionation process of the present invention is utilized, sec-butylethylbenzene is inevitably formed to some extent, usually in a proportion of about 0.1% by weight. Therefore, it is generally inevitable that sec-butylethylbenzene is contained in the product of the disproportionation reaction in a ratio of about 0.1% by weight or more to the total weight of butylethylbenzene.

However, since isobutylethylbenzene is employed as an intermediate for a medicine, the higher its purity is, the better. Thus, needless to say, the contamination of the product with sec-butylethylbenzene which is difficult to separate is not preferable.

Here, assuming that sec-butylethylbenzene and p-isobutylethylbenzene are dehydrogenated, it can be presumed that compounds which will be formed are sec-butylstyrene and p-isobutylstyrene. However, boiling points of these compounds are close to each other, and therefore the separation thereof by distillation is considered to be difficult, as in the case of the disproportionation reaction. In other words, if the products of the disproportionation reaction are difficult to separate by distillation, it seems that the separation of the disproportionated products would be still difficult, even after they have been dehydrogenated. It can also presumed that the secondary reaction in the dehydrogenation step usually makes the separation more difficult.

Now, the present inventors have found that when a mixture of sec-butylethylbenzene and p-isobutylethylbenzene is brought into contact with a dehydrogenation metal catalyst under specific conditions, sec-butylethylbenzene is dehydrogenated and predominantly subjected to secondary reactions of decomposition and the like. On the other hand, p-isobutylethylbenzene is predominantly and exclusively dehydrogenated on the ethyl group thereof. That is, under the dehydrogenation conditions for converting at least p-isobutylethylbenzene into p-isobutylstyrene, p-isobutylstyrene is mainly obtained from the mixture of sec-butylethylbenzene and p-isobutylethylbenzene.

As a result, contrary to the supposition, it has been found that after the contact with the dehydrogenation catalyst, high-purity p-isobutylstyrene not containing any components which cannot be separated by the distillation can be obtained.

However, if sec-butylethylbenzene is present in extremely large quantities in the raw material for the dehydrogenation, it is not easy to separate and recover the produced p-isobutylstyrene in a high purity, even after the dehydrogenation has been done.

For this reason, in the present invention, it is important that the amount of sec-butylethylbenzene in butylethylbenzene which is the raw material for the dehydrogenation does not exceed 20% by weight, preferably 10% by weight to the total weight of butylethylbenzene.

As the solvent for the disproportionation, any solvent can be used, so long as it does not badly affect the disproportionation reaction, the separation and refining of p-isobutylethylbenzene.

The disproportionation reaction can be performed in a gaseous phase or a liquid phase by a batch process or a stream system such as a fixed-bed process, a moving-bed process or a fluidized-bed process.

After the disproportionation reaction of the present invention, if necessary, distillation is made to recover p-isobutylethybenzene in a high purity. In this case, p-isobutylethybenzene can be separated from the position isomers, i.e., m- and o-isobutylethybenzenes by the distillation. As previously described, however, the separation of sec-butylethybenzene by the distillation is limited to a certain level. In the case that the purity of p-isobutylethylbenzene is in a proper range, the disproportionation reaction product can be directly fed to the subsequent dehydrogenation step.

The above-mentioned distillation may be carried out in any manner of vacuum distillation, atmospheric distillation and pressurizing distillation. However, since the desired compound p-isobutylethylbenzene has a relatively high boiling point, and since its deterioration by heat at the distillation should be avoided, the atmospheric distillation or the vacuum distillation are industrially preferable. With regard to a type of distillation column, a tray type or a packed type may be acceptable. Furthermore, with regard to distillation facilities, a continuous distillation apparatus or a batch distillation apparatus is usable. With regard to the distillation precision of the distillation apparatus, a necessary theoretical step number is usually 20 steps or more, preferably 30 steps or more.

The mixture of p-isobutylethylbenzene and sec-butylethylbenzene obtained by the disproportionation reaction and the optional distillation is then brought into contact with a dehyrogenation metal catalyst containing at least one of metal selected from the groups Ib, IIb, VIa, VIIa and VIII of the periodic table in a gaseous phase at a reaction temperature of 300° to 650° C. under a reaction pressure of 50 kg/cm² or less, and if necessary, distillation is then carried out, whereby high-purity p-isobutylstyrene can be recovered.

When brought into contact with the dehydrogenation metal catalyst in accordance with the present invention, most of sec-butylethylbenzene is subjected to a secondary reaction such as decomposition, so that it is converted into compounds having lower molecular weights. On the other hand, p-isobutylethylbenzene is dehydrogenated to mainly become p-isobutylstyrene.

Therefore, the material which has not undergone the dehydrogenation is contaminated with the component which is difficult to separate by the distillation, but the product which has undergone the dehydrogenation is highly pure, i.e., in the refined state.

The dehydrogenation catalyst is the metal catalyst containing at least one metal selected from the groups Ib, IIb, VIa, VIIa and VIII, and typical examples of the metal catalyst include metallic compounds of iron, copper, zinc, nickel, palladium, platinum, cobalt, rhodium, iridium, ruthenium, chromium and molybdenum, and a suitable combination thereof can be also used effectively. The preferable catalyst is what contains at least one metal selected from iron, copper and chromium. These metals can be used singly and in a suitable form such as an oxide, a chloride or a sulfide. In particular, an iron oxide catalyst or a copper-chromium catalyst has a high selectivity for the formation of p-isobutylstyrene, and therefore such a catalyst is effective to accomplish the object of the present invention.

In general, the dehydrogenation catalyst gradually loses its activity owing to coking and the like during using for a long period of time. Therefore, in this case, the catalyst is decoked with air at a high temperature of about 500° C., whereby the initial activity of the catalyst can be recovered. After decoking the catalyst, if necessary, a hydrogen treatment may be carried out by putting the catalyst in a hydrogen stream at a temperature of 200° to 500° C.

The dehydrogenation temperature is from 300° to 650° C., preferably 400° to 650° C., depending upon a composition of the catalyst, a contact time, a dilution molar ratio and the like. When the reaction temperature is higher than this range, not only a decomposition reaction but also a secondary reaction in which produced p-isobutylstyrene is further dehydrogenated increases abruptly, so that the selectivity of p-isobutylstyrene declines noticeably. This fact increases the loss of p-isobutylethylbenzene and complicates the distribution of the products, with the result that it is unpreferably difficult to separate p-isobutylstylene and unreacted p-isobutylethylbenzene by the distillation or the like. When the reaction temperature is less than the above-mentioned range, the reaction rate of dehydrogenation declines noticeably, which is uneconomical.

The olefin produced by the dehydrogenation reaction is polymerizable, and therefore if the olefin remains a high concentration in the reaction phase, the obtained p-isobutylstyrene is partially polymerized to incur a loss. In order to avoid this loss, it is effective to lower the concentration of the olefin gas by diluting the latter with a non-reducing gas such as a nitrogen gas, a helium gas, an argon gas, steam or an oxygen gas. In addition, the dilution can be also made by the use of a solvent such as benzene which is scarcely dehydrogenated. In order to maintain the dehydrogenation activity of the catalyst, the dehydrogenation may be carried out introducing steam into the reaction phase. In this case, the amount of steam is not particularly restrictive.

With regard to a reaction system in the dehydrogenation step, a fixed-bed process, a moving-bed process or a fluidized-bed process can be used to achieve the object of the present invention.

The reaction pressure is not particularly limited, so long as it is in the range capable of vaporizing p-isobutylstyrene produced under the above-mentioned reaction conditions, but the reaction pressure is usually 50 kg/cm² or less, preferably from atmospheric pressure to 10 kg/cm².

The contact time of the raw material p-isobutylethylbenzene with the catalyst is suitably selected from the range of 0.005 to 20 seconds, preferably 0.01 to 10 seconds, more preferably 0.05 to 5 seconds. When the contact time is shorter than the above-mentioned range, reaction ratio lowers unpreferably. Inversely, when the contact time is longer than the above-mentioned range, a secondary reaction such as the further dehydrogenation of produced p-isobutylstyrene increases, so that the selectivity of p-isobutylstyrene lowers unpreferably. The contact time can be suitably changed in the above-mentioned range in compliance with various combinations of the reaction system, the composition of the reaction gas, the composition of the catalyst, the reaction temperature, the preheating temperature of the raw material gas, and the like.

Needless to say, the above-mentioned dehydrogenation process can be carried out by a continuous system or a batch system.

After the contact with the dehydrogenation metal catalyst, distillation can be performed, if necessary. The distillation permits recovering p-isobutylstyrene in a high purity. As described above, p-isobutylstyrene is obtained in a substantially refined state by the dehydrogenation, and hence the dehydrogenated product can be fed to the next process without any particular distillation, depending upon a kind of subsequent reaction.

The thus obtained p-isobutylstyrene will be subjected to hydrocarboxylation by the use of carbon monoxide and water in the presence of a transition metal catalyst, hydroesterification by the use of carbon monoxide and an alcohol, followed by hydrolysis, or hydroformylation, by the use of carbon monoxide and hydrogen to form α-(4-isobutylphenyl)propionaldehyde, followed by oxidizing, whereby α-(4-isobutylphenyl)propionic acid which is useful as a medicine will be able to be easily obtained.

According to the method of the present invention, p-isobutylstyrene having useful applications can be prepared in a high purity from o- and m-isobutylethylbenzenes which have not been heretofore used availably because of novel substances. It is very significant from an industrial viewpoint that the method of the present invention provides high-purity p-isobutylstyrene not contaminated with components which cannot be separated by distillation or the like, seeing that useful applications of p-isobutylstyrene are medicines in which the high purity is required.

Now, the present invention will be described in detail in reference to examples. In these examples, "%" means "% by weight", unless otherwise noted.

EXPERIMENTAL EXAMPLE 1

Synthesis of o-Isobutylethylbenzene

Reference Example

In a 7-liter separable four-necked flask equipped with a stirrer and a reflux condenser were placed 3 liters of sufficiently dried diethyl ether and 245 g of metallic magnesium, and 1,370 g (10 mols) of isobutyl bromide was then slowly added dropwise thereto, while diethyl ether was refluxed. After completion of the addition, diethyl ether was further refluxed with stirring for 1 hour, and the resulting diethyl ether solution of isobutylmagnesium bromide was transferred to a dropping funnel.

In a 15-liter separable four-necked flask equipped with a stirrer and a reflux condenser were placed 3 liters of sufficiently dried diethyl ether, 915 g (5 mols) of o-bromostyrene and 31 g of bis(1,3-diphenylsulfino)-propanenickel(II) chloride, and the above obtained diethyl ether solution of isobutylmagnesium bromide was added dropwise thereto with stirring at room temperature. After completion of the addition, diethyl ether was continuously refluxed with stirring, until the reaction was over. After completion of the reaction, the liquid was cooled to room temperature and was then thrown into ice so as to inactivate isobutylmagnesium bromide. The resulting ether layer was separated by the use of a separatory funnel and was then washed with water until a neutral level was reached. Afterward, the resulting diethyl ether was distilled off, so that 716 g of crude o-isobutylstyrene was obtained.

In a 1-liter autoclave equipped with a stirrer were placed 35.8 g of a 10% palladium black catalyst and the total amount of the above obtained o-isobutylstyrene, and hydrogenation was then carried out at a reaction temperature of 50° C. under a hydrogen pressure of 20 kg/cm$^2$. After hydrogen was not absorbed any more, the reaction mixture was filtered to remove the catalyst, followed by distilling, so that 642 g of o-isobutylethylbenzene having a purity of 99.8% was prepared.

| Physical Properties of o-Isobutylethylbenzene | |
| --- | --- |
| Boiling Point (static method) | 211.1° C. (colorless liquid) |
| Specific Gravity (Ostwald pycnometer method, 15/4° C.) | 0.8724 |
| Refractive Index (N$_{20}$D) | 1.4956 |
| Kinematic Viscosity (40° C.) | 1.46CS |
| Infrared Absorption Spectrum (liquid film method, cm$^{-1}$). | |
| 2960, 1950, 1920, 1850, 1820, 1700, 1610, 1500, 1470, 1390, 1370, 1340, 1290, 1170, 1140, 1080, 1070, 970, 940, 920, 800, 760 | |
| Nuclear Magnetic Resonance Spectrum (CCl$_4$ solvent, δ ppm) | |
| 6.95 | (4H, singlet) |
| 2.3–2.8 | (4H, quartet) |
| 1.5–2.1 | (1H, septet) |
| 1.0–1.4 | (3H, triplet) |
| 0.7–1.0 | (6H, doublet) |
| Mass Spectrum (EI, 70 eV) | |
| m/e | (pattern coefficient) |
| 162 | (31) |
| 133 | (5) |
| 119 | (100) |
| 105 | (14) |
| 91 | (24) |
| 77 | (7) |
| 43 | (5) |
| 29 | (2) |
| Elementary Analysis (as C$_{12}$H$_{18}$) | |
| Calcd. | C: 88.89 |
| | H: 11.11 |
| Found | C: 88.92 |
| | H: 10.97 |

EXPERIMENTAL EXAMPLE 2

Synthesis of m-Isobutylethylbenzene

In a 7-liter separable four-necked flask equipped with a stirrer and a reflux condenser were placed 3 liters of sufficiently dried diethyl ether and 245 g of metallic magnesium, and 1,370 g (10 mols) of isobutyl bromide was then slowly added dropwise thereto, while diethyl ether was refluxed. After completion of the addition, diethyl ether was further refluxed with stirring for 1 hour, and the resulting diethyl ether solution of isobutylmagnesium bromide was transferred to a dropping funnel.

In a 15-liter separable four-necked flask equipped with a stirrer and a reflux condenser were placed 3 liters of sufficiently dried diethyl ether, 915 g (5 mols) of m-bromostyrene and 31 g of bis(1,3-diphenylsulfino)-propane-nickel(II) chloride, and the above obtained diethyl ether solution of isobutylmagnesium bromide was added dropwise thereto with stirring at room temperature. After completion of the addition, diethyl ether was continuously refluxed with stirring, until the reaction was over. After completion of the reaction, the liquid was cooled to room temperature and was then thrown into ice so as to inactivate isobutylmagnesium bromide. The resulting ether layer was separated by the use of a separatory funnel and was then washed with water until a neutral level was reached. Afterward, the resulting diethyl ether was distilled off, so that 670 g of crude m-isobutylstyrene was obtained.

In a 1-liter autocalve equipped with a stirrer were placed 33.5 g of a 10% palladium black catalyst and the total amount of the above obtained crude m-isobutylstyrene, and hydrogenation was then carried out at a reaction temperature of 50° C. under a hydrogen pressure of 20 kg/cm². After hydrogen was not absorbed any more, the reaction mixture was filtered to remove the catalyst, followed by distilling, so that 617 g of m-isobutylethylbenzene having a purity of 99.7%.

| Physical Properties of m-Isobutylethylbenzene | |
|---|---|
| Boiling Point (static method) | 210.8° C. (colorless liquid) |
| Specific Gravity (Ostwald pycnometer method, 15/4° C.) | 0.8583 |
| Refractive Index ($N_{20}D$) | 1.4884 |
| Kinematic Viscosity (40° C.) | 1.29CS |
| Infrared Absorption Spectrum (liquid film method, $cm^{-1}$), | |
| 2960, 1940, 1860, 1800, 1700, 1620, 1590, 1500 1470, 1390, 1370, 1340, 1290, 1220, 1180, 1110, 1090, 1070, 1060, 890, 820, 790, 740, 710 | |
| Nuclear Magnetic Resonance Spectrum ($CCl_4$ solvent, δ ppm) | |
| 6.95 | (4H, singlet) |
| 2.3–2.8 | (4H, quartet) |
| 1.5–2.1 | (1H, septet) |
| 1.0–1.4 | (3H, triplet) |
| 0.7–1.0 | (6H, doublet) |
| Mass Spectrum (EI, 70 eV) | |
| m/e | (pattern coefficient) |
| 162 | (35) |
| 133 | (2) |
| 119 | (100) |
| 105 | (19) |
| 91 | (24) |
| 77 | (6) |
| 43 | (7) |
| 29 | (2) |
| Elementary Analysis (as $C_{12}H_{18}$) | |
| Calcd. | C: 88.89 |
|  | H: 11.11 |
| Found | C: 88.91 |
|  | H: 10.99 |

EXPERIMENTAL EXAMPLE 3

Preparation of p-Isobutylethylbenzene

Disproportionation Reaction 1

In a 3-liter autoclave equipped with a stirrer were placed 600 g of o-isobutylethylbenzene obtained in Experimental Example 1, 1,200 g of isobutylbenzene having a purity of 99.8% and 90 g of the silica-alumina catalyst N633L (trade name; made by Nikki Kagaku Co., Ltd.), and the gaseous portion in the system was then replaced with nitrogen. Afterward, the autoclave was hermetically closed and then heated up to 270° C. in order to carry out disproportionation reaction for 24 hours. After completion of the reaction, the used catalyst was removed out by filtration, and the reaction mixture was then analyzed through gas chromatography. The composition of the reaction mixture is set forth in Table 1.

TABLE 1

| Isobutylbenzene | 59.2% by weight |
|---|---|
| sec-Butylbenzene | 1.2% by weight |
| o-Isobutylethylbenzene | 7.8% by weight |
| m-Isobutylethylbenzene | 12.3% by weight |
| p-Isobutylethylbenzene | 7.9% by weight |
| sec-Butylethylbenzene | 0.6% by weight |
| Others | 11.0% by weight |

Furthermore, the conversion of o-isobutylethylbenzene was 76.6%, and the selectivity of p-isobutylethylbenzene was 31.0%.

EXPERIMENTAL EXAMPLE 4

Preparation of p-Isobutylethylbenzene

Disproportionation Reaction 2

In a 3-liter autoclave equipped with a stirrer were placed 600 g of m-isobutylethylbenzene obtained in Experimental Example 2, 1,200 g of isobutylbenzene having a purity of 99.8% and 90 g of the silica-alumina catalyst N633L (trade name; made by Nikki Kagaku Co., Ltd.), and the gaseous portion in the system was then replaced with nitrogen. Afterward, the autoclave was hermetically closed and then heated up to 270° C. in order to carry out disproportionation reaction for 24 hours. After completion of the reaction, the used catalyst was removed out by filtration, and the reaction mixture was then analyzed through gas chromatography. The composition of the reaction mixture is set forth in Table 2.

TABLE 2

| Isobutylbenzene | 58.9% by weight |
|---|---|
| sec-Butylbenzene | 1.3% by weight |
| o-Isobutylethylbenzene | 6.7% by weight |
| m-Isobutylethylbenzene | 15.4% by weight |
| p-Isobutylethylbenzene | 6.0% by weight |
| sec-Butylethylbenzene | 0.6% by weight |
| Others | 11.1% by weight |

Furthermore, the conversion of m-isobutylethylbenzene was 53.7%, and the selectivity of p-isobutylethylbenzene was 22.6%.

EXPERIMENTAL EXAMPLE 5

Disproportionation Reaction 3

In a 3-liter autoclave equipped with a stirrer were placed 600 g of an equivalent mixture of m- and o-isobutylethylbenzenes obtained in Experimental Examples 1 and 2, 1,200 g of isobutylbenzene having a purity of 99.8% and 90 g of silica-alumina catalyst N633L (trade name; made by Nikki Kagaku Co., Ltd.), and the gaseous portion in the system was then replaced with nitrogen. Afterward, the autoclave was hermetically closed and then heated up to 270° C. in order to carry out disproportionation reaction for 24 hours. After completion of the reaction, the used catalyst was removed out by filtration, and the reaction mixture was then analyzed through gas chromatography. The composition of the reaction mixture is set forth in Table 3.

TABLE 3

| Isobutylbenzene | 60.3% by weight |
|---|---|
| sec-Butylbenzene | 1.3% by weight |
| o-Isobutylethylbenzene | 6.0% by weight |
| m-Isobutylethylbenzene | 15.8% by weight |

TABLE 3-continued

| | |
|---|---|
| p-Isobutylethylbenzene | 6.7% by weight |
| sec-Butylethylbenzene | 0.7% by weight |
| Others | 10.5% by weight |

In a 2-liter three-necked flask was placed 1,000 g of the above obtained reaction mixture, and the latter was then distilled on a batch system in a reflux ratio of 20 by the use of a distillation column having 35 theoretical steps in which a glass pipe having an inner diameter of 30 mm and a length of 1.5 m was packed with Heli Pack No. 3 metal (trade name) made by Tokyo Tokushu Kanaami Co., Ltd., in order to prepare 43.4 g of a fraction in which the purity of p-isobutylethylbenzene was 97.2% (recovery 63.0%, and the content of sec-butylethylbenzene in the total butylethylbenzene was 1.9%).

EXPERIMENTAL EXAMPLE 6

Disproportionation Reaction 4

In a 1-liter autoclave were placed 500 g of a mixture of components in Table 4 and 25 g of trifluoromethanesulfonic acid having a purity of 99% by weight, and disproportionation reaction was carried out with stirring at 110° C. for 24 hours. Afterward, the reaction mixture was neutralized with Ca(OH)$_2$ and was then washed with water. The resulting organic phase was then analyzed through gas chromatography. The results are set forth in Table 5.

TABLE 4

| | |
|---|---|
| Isobutylbenzene | 81.8% by weight |
| Isobutylethylbenzene | 14.2% by weight |
| o- | 7.5% by weight |
| m- | 5.5% by weight |
| p- | 1.2% by weight |
| Isobutyldiethylbenzene | 3.4% by weight |
| Others | 0.5% by weight |

TABLE 5

| | |
|---|---|
| Isobutylbenzene | 78.7% by weight |
| sec-Butylbenzene | 1.8% by weight |
| Isobutylethylbenzene | 15.1% by weight |
| o- | 3.1% by weight |
| m- | 7.3% by weight |
| p- | 4.7% by weight |
| sec-Butylethylbenzene | 0.4% by weight |
| Isobutyldiethylbenzene | 2.9% by weight |
| Others | 1.1% by weight |

In a 1-liter three-necked flask was placed this disproportionated reaction mixture, and the latter was then distilled in the same manner as in Experimental Example 5 in order to prepare 16 g of a fraction in which the purity of p-isobutylethylbenzene was 97% by weight or more (recovery 68.1%, and the content of sec-butylethylbenzene in the total butylethylbenzene was 2.2%).

EXPERIMENTAL EXAMPLE 7

Disproportionation Reaction 5

As in Experimental Example 5, in a 1-liter autoclave were placed 500 g of a mixture of components in Table 4 mentioned above and 25 g of hydrogen fluoride having a purity of 99.7% by weight, and disproportionation reaction was carried out with stirring at 110° C. for 24 hours. Afterward, the reaction mixture was neutralized with Ca(OH)$_2$ and was then washed with water. The resulting organic phase was then analyzed through gas chromatography. The results are set forth in Table 6.

TABLE 6

| | |
|---|---|
| Isobutylbenzene | 78.5% by weight |
| sec-Butylbenzene | 1.7% by weight |
| Isobutylethylbenzene | 15.7% by weight |
| o- | 3.9% by weight |
| m- | 7.2% by weight |
| p- | 4.6% by weight |
| sec-Butylethylbenzene | 0.4% by weight |
| Isobutyldiethylbenzene | 2.7% by weight |
| Others | 1.0% by weight |

In a 1-liter three-necked flask was placed this disproportionated reaction mixture, and the latter was then distilled in the same manner as in Experimental Example 5 in order to prepare 15 g of a fraction in which the purity of p-isobutylethylbenzene was 97% by weight or more (recovery 65.2%, and the content of sec-butylethylbenzene in the total butylethylbenzene was 2.0%).

EXPERIMENTAL EXAMPLE 8

Disproportionation Reaction 6

As in Experimental Example 5, in a 1-liter autoclave were placed 500 g of a mixture of components in Table 4 mentioned above and 25 g of HY Zeolite, and disproportionation reaction was then carried out with stirring at 180° C. for 24 hours. Afterward, the used catalyst was removed from the reaction mixture by filtration. The resulting organic phase was then analyzed through gas chromatography. The results are set forth in Table 7.

TABLE 7

| | |
|---|---|
| Isobutylbenzene | 77.2% by weight |
| sec-Butylbenzene | 0.5% by weight |
| Isobutylethylbenzene | 19.4% by weight |
| o- | 0.3% by weight |
| m- | 12.0% by weight |
| p- | 7.1% by weight |
| sec-Butylethylbenzene | 0.1% by weight |
| Isobutyldiethylbenzene | 0.2% by weight |
| Others | 2.6% by weight |

In a 1-liter three-necked flask was placed this disproportionated reaction mixture, and the latter was then distilled in the same manner as in Experimental Example 5 in order to prepare 25 g of a fraction in which the purity of p-isobutylethylbenzene was 97% by weight or more (recovery 70.4%, and the content of sec-butylethylbenzene in the total butylethylbenzene was 0.5%).

EXPERIMENTAL EXAMPLE 9

Disproportionation Reaction 7

As in Experimental Example 5, in a 1-liter autoclave were placed 500 g of a mixture of components in Table 4 mentioned above and 25 g of phosphotungstic acid, and disproportionation reaction was carried out with stirring at 250° C. for 24 hours. Afterward, the used catalyst was removed from the reaction mixture by filtration. The resulting organic phase was then analyzed through gas chromatography. The results are set forth in Table 8.

TABLE 8

| | |
|---|---|
| Isobutylbenzene | 77.8% by weight |
| sec-Butylbenzene | 1.9% by weight |
| Isobutylethylbenzene | 15.4% by weight |
| o- | 2.7% by weight |
| m- | 7.1% by weight |

TABLE 8-continued

| | |
|---|---|
| p- | 5.6% by weight |
| sec-Butylethylbenzene | 0.4% by weight |
| Isobutyldiethylbenzene | 2.9% by weight |
| Others | 1.6% by weight |

In a 1-liter three-necked flask was placed this disproportionated reaction mixture, and the latter was then distilled in the same manner as in Experimental Example 5 in order to prepare 19 g of a fraction in which the purity of p-isobutylethylbenzene was 97% by weight or more (recovery 67.9%, and the content of sec-butylethylbenzene in the total butylethylbenzene was 2.2%).

EXPERIMENTAL EXAMPLE 9A

Disproportionation Reaction 8

As in Experimental Example 5, in a 1-liter autoclave were placed 500 g of a mixture of components in Table 4 mentioned above and 30 g of Nafion resin pellets (trade name, made by Du Pont Co.), and disproportionation reaction was carried out with stirring at 180° C. for 24 hours. Afterward, the used catalyst was removed from the reaction mixture by filtration. The resulting organic phase was then analyzed through gas chromatography. The results are set forth in Table 8a.

TABLE 8a

| | |
|---|---|
| Isobutylbenzene | 77.4% by weight |
| sec-Butylbenzene | 1.4% by weight |
| Isobutylethylbenzene | 15.4% by weight |
| o- | 2.0% by weight |
| m- | 7.6% by weight |
| p- | 5.8% by weight |
| sec-Butylethylbenzene | 0.3% by weight |
| Isobutyldiethylbenzene | 2.6% by weight |
| Others | 2.9% by weight |

In a 1-liter three-necked flask was placed this disproportionated reaction mixture, and the latter was then distilled in the same manner as in Experimental Example 5 in order to prepare 20 g of a fraction in which the purity of p-isobutylethylbenzene was 97% by weight or more (recovery 69.0%, and the content of sec-butylethylbenzene was 1.9%).

EXPERIMENTAL EXAMPLE 10

Ethylation and Disproportionation

In a 10-liter autoclave were placed 6,000 ml of isobutylbenzene having a purity of 99.8% by weight and 260 g of silica-alumina catalyst IS-28 (trade name; made by Shokubai Kasei Co., Ltd.), and the system was then heated with stirring up to 250° C. Afterward, ethylene was fed thereto, and reaction was then performed for 12 hours, while pressure was maintained at 20 kg/cm². After completion of the reaction, the used catalyst was removed therefrom by filtration. Analysis was then made by the use of gas chromatography. The composition of the reaction mixture is set forth in Table 9.

TABLE 9

| | |
|---|---|
| Isobutylbenzene | 80.1% by weight |
| sec-Butylbenzene | 1.1% by weight |
| Isobutylethylbenzene | 14.3% by weight |
| o- | 5.7% by weight |
| m- | 4.4% by weight |
| p- | 4.2% by weight |
| sec-Butylethylbenzene | 0.2% by weight |
| Others | 4.3% by weight |

As a result, the conversion of isobutylbenzene was 19.7% by weight, a ratio of mols of the produced p-isobutylethylbenzene to mols of consumed isobutylbenzene (hereinafter referred to as "selectivity of p-isobutylethylbenzene") was 17.6%, and the position isomers of isobutylethylbenzene were present in a ratio of ortho:meta:para=40:31:29.

Next, 5742 g of this ethylated reaction mixture was distilled in the same manner as in Experimental Example 5 in order to obtain 188 g of a fraction in which the purity of p-isobutylethylbenzene was 97.3% (recovery 75.9%).

Afterward, all of the fraction which was left after p-isobutylethylbenzene had been recovered from the ethylated reaction mixture was subjected to disproportionation reaction with 267 g of HY zeolite at 180° C. for 24 hours, and 5550 g of the resulting reaction mixture (p-isobutylethylbenzene content was 4.6% by weight) was then distilled in order to prepare 209 g of a fraction in which the purity of p-isobutylethylbenzene was 97.1%.

EXPERIMENTAL EXAMPLE 11

Preparation of p-Isobutylstyrene

Dehydrogenation Reaction 1

An iron oxide dehydrogen catalyst G-64A (trade name; Nissan Gardlar Co., Ltd.) containing potassium and chromium as co-catalysts was prepared so that its grain diameter might be in the range of 1 mm to 2 mm, and a stainless steel pipe having an inner diameter of 12 mm and a length of 1 m was filled with 20 ml of the catalyst.

The same procedure as in Experimetal Example 5 was repeated to obtain p-isobutylethylbenzene fraction, and 100 g of this p-isobutylethylbenzene was passed through a preheating pipe and then through the catalyst layer at a reaction temperature of 550° C. at a flow rate of 10 ml/hour together with water at a flow rate of 90 ml/hour in order to perform dehydrogenation (contact time with the catalyst was 0.2 second, and a molar ratio of stream to the p-isobutylethylbenzene fraction was 93). The thus dehydrogenated material was cooled, and a gas and water were then separated out therefrom. Afterward, the resulting organic phase was analyzed through gas chromatography. The composition of the resulting organic phase is set forth in Table 10.

TABLE 10

| | |
|---|---|
| p-Isobutylethylbenzene | 69.1% by weight |
| p-Isobutylstyrene | 23.2% by weight |
| Others | 7.7% by weight |

Furthermore, the conversion of p-isobutylethylbenzene was 28.9%, and the selectivity of p-isobutylstyrene was 82.6%.

In a 500-milliliter three-necked flask were placed 90 g of the above obtained organic phase and 300 g of silicone oil as a flux oil, and distillation was then carried out by the same batch system as in Experimental Example 5 in order to prepare a fraction in which the purity of p-isobutylstyrene was 98.7%. In this fraction, a compound corresponding to dehydrogenated sec-butylethylbenzene was present in an amount of 0.3%.

That is, it is apparent that the purity of p-isobutylstyrene which is the compound corresponding to the raw material p-isobutylethylbenzene increases after the reaction.

EXPERIMENTAL EXAMPLES 12 TO 16

The same raw material as in Experimental Example 11 was dehydrogenated in the same procedure as in Experimental Example 11 with the exception that a copper-chromium dehydrogenation catalyst was used which was composed of 18% by weight of $Cr_2O_3$, 39% by weight of CuO and 38% by weight of ZnO. After completion of the dehydrogenation reaction, distillation was performed in the same manner as in Experimetal Example 11. The results are set forth in Table 11.

TABLE 11

| Experimental Example | 12 | 13 | 14 | 15 | 16 |
|---|---|---|---|---|---|
| Reaction Temperature (°C.) | 450 | 500 | 550 | 600 | 650 |
| Contact Time (second) | 0.2 | 0.2 | 0.2 | 0.2 | 0.2 |
| Molar Ratio of Steam | 93 | 93 | 94 | 93 | 93 |
| Conversion of PBE (%) | 2 | 6 | 12 | 21 | 45 |
| Selectivity of PBS (%) | 78 | 76 | 72 | 64 | 47 |
| Purity of PBS (%) | 98.4 | 98.6 | 98.8 | 98.5 | 98.1 |
| Conc. of Compound Corresponding to Dehydrogenated sec-Butylbenzene (%) | 0.7 | 0.5 | 0.5 | 0.4 | 0.4 |

EXPERIMENTAL EXAMPLE 17

Following the same procedure as in Experimental Example 11 with the exception that the metal of the dehydrogenation metallic catalyst was replaced with each of metals shown in the following table, the p-isobutylethylbenzene fraction was dehydrogenated. These metals were all used in the form of oxides, and the latter were supported on silica carriers. After reaction, distillation was performed as in Experimental Example 11. The results are set forth in Table 12.

TABLE 12

| | Results of Dehydrogenation | | Results of Distillation | |
|---|---|---|---|---|
| Metal | Conversion (%) | Selectivity (%) | Purity of PBS (%) | Conc. of Compound Corresponding to Dehydrogenated sec-Butylethylbenzene (%) |
| Ag | 31 | 62 | 98.6 | 0.4 |
| Cd | 12 | 64 | 98.4 | 0.6 |
| Cr | 22 | 61 | 98.4 | 0.6 |
| Zn | 13 | 52 | 98.7 | 0.4 |
| Mo | 16 | 53 | 98.8 | 0.3 |
| W | 11 | 59 | 98.8 | 0.3 |
| Mn | 11 | 61 | 98.3 | 0.5 |
| Tc | 12 | 60 | 98.6 | 0.4 |
| Re | 20 | 57 | 98.1 | 0.7 |
| Ru | 17 | 68 | 98.2 | 0.5 |
| Os | 12 | 70 | 98.7 | 0.4 |
| Co | 21 | 59 | 98.2 | 0.6 |
| Rh | 32 | 48 | 98.0 | 0.8 |
| Ir | 25 | 51 | 98.1 | 0.6 |
| Ni | 48 | 41 | 97.9 | 0.9 |
| Pd | 46 | 43 | 98.2 | 0.7 |
| Pt | 44 | 40 | 98.2 | 0.6 |

EXPERIMENTAL EXAMPLE 18

Preparation of Methyl α-(4-Isobutylphenyl)propionate

Hydroesterification Reaction Reference Example

In a 200-milliliter autoclave equipped with a stirrer were placed 25.0 g of p-isobutylstyrene having a purity of 98.7% obtained by distillation in Experimental Example 11, 10.0 ml of methanol, 100 ml of toluene as a solvent, 0.0271 g of $PdCl_2$ as a catalyst, 0.0105 g of $CuCl_2$ as a co-catalyst and 0.0812 g of triphenylphosphine as a ligand, and they were heated up to 90° C. with stirring. Aferward, pressure was maintained at 70 kg/cm² by carbon monoxide to perform reaction for 8 hours. After completion of the reaction, the reaction mixture was cooled and then analyzed by gas chromatography. As a result, the conversion of p-isobutylstyrene was 99.8%, and the selectivity of methyl α-(4-isobutylphenyl)propionate was 90.2%.

EXPERIMENTAL EXAMPLE 19

Preparation of α-(4-Isobutylphenyl)propionic acid

Hydrolysis Reaction Reference Example

Fifteen grams of methyl α-(4-isobutylphenyl)propionate obtained by distilling the reaction mixture of Experimental Example 18 and 75 ml of a 10% aqueous sodium hydroxide solution were refluxed with stirring in order to perform hydrolysis for about 3 hours. After cooling, the mixture was allowed to stand, and a separated aqueous lower layer was washed with n-hexane.

To the aqueous layer was added 5% hydrochloric acid so as to adjust its pH to 2, and a separated oil portion was extracted with n-hexane and washed with water. n-Hexane was then vaporized under reduced pressure and separated out in order to prepare 12.0 g of light yellow crude α-(4-isobutylphenyl)propionic acid crystals.

This crude α-(4-isobutylphenyl)propionic acid was recrystallized from a n-hexane solvent in order to prepare 10.4 g of white refined α-(4-isobutylphenyl)propionic acid crystals (melting point 75°–76° C.). The melting point and spectra of the product were coincident with standards.

What is claimed is:

1. A method for preparing a high purity p-isobutylstyrene which comprises a first step of reacting o- and/or m-isobutylethylbenzene in the presence of a disproportionation acid catalyst at a reaction temperature of −10° C. to 600° C. whereby a mixture of p-isobutylethylbenzene and sec-butylethylbenzene are produced in a concentration such that the sec-butylethylbenzene represents between about 0.1% and 20% by weight, based on the total weight of the butylethylbenzene product;

and a second step of contacting said mixture of p-isobutylethylbenzene and sec-butylethylbenzene, recovered from said first step, with a dehydrogenation metal catalyst containing at least one metal selected from the group consisting of metals of Group Ib, Group IIb, Group IVa, Group VIIa and Group VIII of the Periodic Table of the Elements at a reaction temperature of 300° C. to 650° C. under a reaction pressure of not more than 50 kg/cm$^2$, said dehydrogenation reaction occurring in the gaseous state.

2. A method in accordance with claim 1 wherein said disproportionation acid catalyst is a solid acid catalyst.

3. A method in accordance with claim 1 wherein said disproportionation acid catalyst is a Friedel-Crafts catalyst.

4. A method in accordance with claim 1 wherein said disproportionation acid catalyst is an organic acid.

5. A method in accordance with claim 1 wherein said disproportionation acid catalyst is an inorganic acid.

6. A method in accordance with claim 1 wherein said disproportionation acid catalyst is a heteropoly-acid.

7. A method in accordance with claim 1 wherein said disproportionation acid catalyst is a strong acid type cation exchange resin.

8. A method in accordance with claim 2 wherein said solid acid catalyst is selected from the group consisting of silica-alumina, zeolite and mixtures thereof.

9. A method in accordance with claim 4 wherein said organic acid is trifluoromethanesulfonic acid.

10. A method in accordance with claim 5 wherein said inorganic acid is hydrogen fluoride.

11. A method in accordance with claim 6 wherein said heteropoly-acid is phosphotungstic acid.

12. A method in accordance with claim 7 wherein said strong acid type cation exchange resin is perfluorosulfonic acid resin.

13. A method in accordance with claim 1 wherein said concentration of sec-butylethylbenzene in said product of said first step is in the range of between about 0.1% and 10% by weight, based on the total weight of the butylethylbenzene product.

14. A method in accordance with claim 1 wherein said dehydrogenation metal catalyst is a metal compound the metal of which is selected from the group consisting of iron, copper, zinc, nickel, palladium, platinum, cobalt, rhodium, iridium, ruthenium, chromium and molybdenum.

15. A method in accordance with claim 14 wherein said dehydrogenation metal catalyst is selected from the group consisting of an iron oxide catalyst and a copper-chromium catalyst.

* * * * *

UNITED STATES PATENT AND TRADEMARK OFFICE
CERTIFICATE OF CORRECTION

PATENT NO.   : 5,436,402
DATED        : July 25, 1995
INVENTOR(S)  : Isoo Shimizu, et al.

It is certified that error appears in the above-indentified patent and that said Letters Patent is hereby corrected as shown below:

Column 2, line 29: "dispropornation" should read --disproportionation--

Signed and Sealed this

Eighth Day of October, 1996

*Attest:*

BRUCE LEHMAN

*Attesting Officer*      *Commissioner of Patents and Trademarks*

UNITED STATES PATENT AND TRADEMARK OFFICE
CERTIFICATE OF CORRECTION

PATENT NO. : 5,436,402
DATED : July 25, 1995
INVENTOR(S) : Isoo Shimizu, et al.

It is certified that error appears in the above-indentified patent and that said Letters Patent is hereby corrected as shown below:

Column 1, lines 19-20: "dispropornation" should read --disproportionation--

Column 3, line 50: "invetnion" should read --invention--

Column 3, line 54: "dispropotionation" should read --disproportionation--

Column 14, line 34: "Experimetal" should read --Experimental--

Signed and Sealed this

Eighteenth Day of February, 1997

Attest:

BRUCE LEHMAN

*Attesting Officer*  *Commissioner of Patents and Trademarks*